United States Patent [19]

Basta et al.

[11] Patent Number: 5,171,663
[45] Date of Patent: Dec. 15, 1992

[54] MONOCLONAL ANTIBODY AGAINST REGULATORY PROTEIN, SGP 120

[75] Inventors: Milan Basta, Rockville; Carl H. Hammer, Gaithersburg; Michael M. Frank, Bethesda, all of Md.

[73] Assignee: The United Stated of America as represented by the Secretary of the Department of Health and Human Services, Washington, D.C.

[21] Appl. No.: 365,772

[22] Filed: Jun. 14, 1989

[51] Int. Cl.$^5$ ............................................. G01N 33/53
[52] U.S. Cl. ............................... 435/7.1; 435/240.27; 435/960; 435/975; 436/518; 436/548; 530/388.7; 530/412
[58] Field of Search ............... 436/548, 518, 531, 808; 935/89, 106; 435/7, 172.2, 240.27, 7.92, 975, 7.1; 530/387, 412; 422/68.1

[56] References Cited

PUBLICATIONS

Hammer et al., "Isolation and Characterization of a Novel Plasma Protein Which Binds to Activated C4 of the Classical Complement Pathway" J. Biol. Chem. 264(4):2283–2291 (Feb. 5, 1989).

Köhler and Milstein, "Continuous Cultures of Fused Cells Secreting Antibody of Predefined Specificity" Nature 256:495–497. (1975).

Sevier et al., "Monodonal Antibodies in Clinical Immunology" Clin. Chem. 27(11):1797–1806 (1981).

Primary Examiner—Esther L. Kepplinger
Assistant Examiner—Carol E. Bidwell
Attorney, Agent, or Firm—Cushman, Darby & Cushman

[57] ABSTRACT

Monoclonal antibodies against complement regulatory protein sgp 120 are provided.

6 Claims, 1 Drawing Sheet

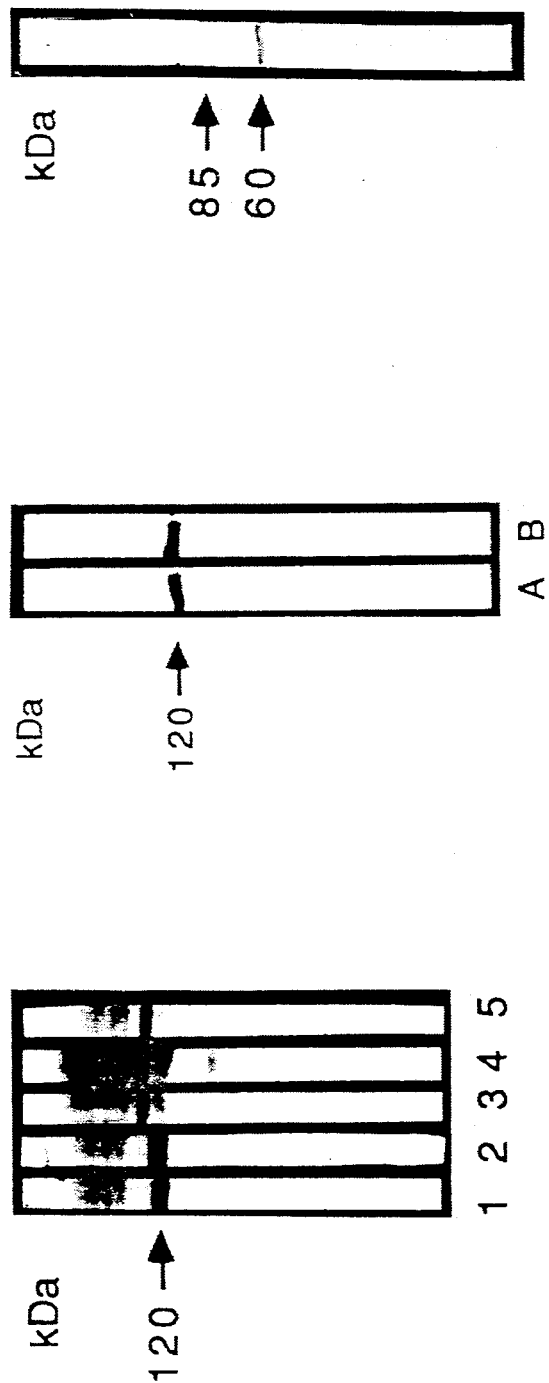

MONOCLONAL ANTIBODY AGAINST REGULATORY PROTEIN, SGP 120

The present invention is related to providing unique monoclonal antibodies which specifically bind to complement regulatory plasma sialoglycoprotein of about 120 kDa molecular weight which is herein referred to as sgp 120. The nature and properties of sgp 120 have been described by Hammer et al, 1989, *J. Biol. Chem.* 264:2283-2291.

As determined by quantitative Mancini test and Dot blot assay, the concentration of sgp 120 in plasma is about 300 µg/ml. It binds to cell-bound C4b and coelutes with C2 from C4b Sepharose from which it is purified. N-terminal amino acid sequence studies have confirmed the uniqueness of sgp 120 protein. It plays a significant complement regulatory role. The intact purified protein inhibits, in a dose responsive and reversible manner, functional hemolytic activity of the classical complement pathway at multiple steps, such as formation of C1, C4, C2 and C3 sites. The protein is initially cleaved by kallikrein into 85 kDa and 35 kDa fragments; the 85 kDa fragment is further cleaved into 60 kDa and 25 kDa fragments. Cleaved sgp 120 causes increased vascular permeability when injected intradermaly into normal guinea pigs. The 85 kDa and 60 kDa fragments share the same N-terminal sequence of amino acids as the intact protein.

Heretofore, a monoclonal antibody reagent against sgp 120 had not been known or described.

SUMMARY OF THE INVENTION

It is, therefore, an object of the present invention to provide anti-sgp 120 monoclonal antibodies.

It is a further object of the present invention to provide methods for purification, detection, localization and inactivation of sgp 120.

Other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 1 demonstrates specificity of antibody-producing clones by Western blotting. Following three separate cell fusions, five antibody-producing clones were identified by ELISA. Western blotting of the culture supernatants of these clones (using Immobilon strips to which human plasma proteins were transblotted from an SDS gel) showed that two clones (lanes 1 and 2) reacted with sgp 120, while the remaining clones (lanes 3, 4, and 5) produced antibodies that bound to a protein of approximately 130 kDa molecular weight.

FIG. 2 demonstrates Western blot analysis of anti-sgp 120 monoclonal antibody reactivity. Human plasma proteins were electrophoretically separated, transblotted onto Immobilon membrane and incubated with B1.9.E-2 culture supernatant (A) and IgG purified from ascites (B). As shown, the monoclonal antibody reacted only with sgp 120.

FIG. 3 demonstrates reactivity of B1.9.E-2 with sgp 120 fragments. Purified sgp 120 was cleaved with kallikrein, fragments separated by SDS-PAGE and blotted onto Immobilon membrane which was subsequently incubated with purified monoclonal IgG at 1:2,000 dilution. The monoclonal antibody showed reactivity with 85 kDa and 60 kDa fragments.

DETAILED DESCRIPTION OF THE INVENTION

The above and various other objects and advantages are achieved by providing the novel anti-sgp 120 monoclonal antibodies of the present invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art. The materials, methods and examples are illustrative only and not limiting.

The abbreviations used herein are as follows: EDTA=ethylenediaminetetraacetic acid; NPGB=p-nitrophenylguanidino-benzoate; SBTI=soybean trypsin inhibitor; GVBS=gelatin-containing veronal-buffered saline; PEG=polyethyleneglycol; and PBS=phosphate-buffered saline.

The term "substantially pure" as used herein means that the product is as pure as can be obtained by standard purification techniques by one of ordinary skill in the art to which this invention belongs.

MATERIALS AND METHODS

Animals. Female Balb/C mice (Jackson Laboratory, Bar Harbor, ME) were used at the age of 8 weeks.

Antigen. sgp 120 was purified according to a modification of the procedure of Hammer et al, supra. Briefly, freshly drawn blood was anti-coagulated with EDTA/NPGB/SBTI solution. sgp 120 was precipitated from plasma with 7.4% to 21.6% (W/V) PEG. Resolubilized protein was applied to a C4b Sepharose column and eluted with GVBS at 15 mS. The 25% PEG cut of the C4b Sepharose eluate was resolubilized and applied to a DEAE-Sephacel column. Recovery of sgp 120 from the column was achieved with a linear salt gradient from 5.6 mS to 15 mS. The protein was about 95% pure as determined by densitometric analysis of an SDS-PAGE gel under non-reducing conditions.

Immunizations. The amount of antigen for each immunization was about 50 µg/mouse. Three mice were each injected four times at 15-day intervals. The antigen (emulsified with an equal volume of complete Freund's adjuvant) for the first two injections was administered subcutaneously, followed by an intraperitoneal injection of the antigen in incomplete Freund's adjuvant. The mice were bled and tested for anti-sgp 120 reactivity by Western blot technique. The last boost (filter-sterilized sgp 120 in PBS) was given by i.v. injection into the tail vein, three days before the fusion.

Fusion. Immunized mice were killed by cervical dislocation and the spleens were removed aseptically. Splenocyte suspension was obtained by perfusing the spleens with the medium (vide infra) through a 25 G needle stuck into the upper pole of the spleen. Mouse lymphocytes were isolated by passing the splenocyte suspension over Lympholyte M solution (Catalog #

CL5030, Cedarline Laboratories). Non-secreting myeloma cells Sp2/0 (American Type Culture Collection, Rockville, Md.) in exponential growth phase and over 95% viable, were used as a fusion partner. The isolated primed lymphocytes were subsequently mixed with myeloma cells at a ratio of 1:8 (myeloma cells: lymphocytes) and fused in 50% (w/v) polyethyleneglycol M.W. 1,500 (Aldrich Chemical Company, Inc., Milwaukee, Wis.). The suspended cells were then plated out in 5 flatbottomed microtiter plates (Nunc, Roskilde, Denmark) in a 200 µl/well volume in HAT medium together with $65 \times 10^6$ fresh Balb/c thymocytes/ml. The plates were incubated at 37° C. in 5% $CO_2$ and screened microscopically for growing clones every day after the seventh day of culture. Ten days after the fusion, the cell culture supernatants were tested for specific reactivity against the immunogen by ELISA assay. Antibody producing hybridomas were transferred to 24 well plates. The clones were grown in larger wells until hybridomas covered the whole bottom of the well. Then, 100 µl samples of supernatants were collected and tested by Western blot. One of the clones was subcloned by means of two subsequent limiting dilutions at a concentration of about 0.5 cells/well. The remaining positive clones were frozen in DMSO medium at −70° C. The subcloned cell line was expanded and grown as ascites tumor in the pristane-primed peritoneal cavities of Balb/c mice. IgG was purified from ascites by octanoic acid precipitation and using FPLC chromatography (MonoQ, ion-exchange column).

Elisa Assay. 96-well microtiter plates were coated overnight (about 12–16 hrs) at 4° C. with 100 µl of carbonate buffer pH=9.6 containing 15 µg/ml of purified sgp 120. Unreacted sites were blocked with 1% BSA in PBS containing 0.05% Tween 20 for 5 hours at room temperature (about 22°–24° C.). After 3 washes with PBS/Tween, 100 µl of hybridoma supernatants diluted 1:10 in PBS was added and incubated for 1 hour at RT (room temperature). The wells were washed three times with PBS/Tween and then incubated with peroxidase conjugated rabbit anti-mouse immunoglobulins. After five washes in PBS/Tween, the quantitation of bound enzyme was performed by incubation with ABTS peroxidase substrate (Kirkegaard and Perry Laboratories, Inc., Gaithersburg, Mass.). The absorbance values were determined in a Titertek Multiscan spectrophotometer.

Determination of monoclonal antibody Ig class and subclass. Class and subclass of the monoclonal antibody were determined by ELISA assay using monospecific rabbit antibodies against mouse $IgG_1$, $IgG_{2a}$, $IgG_{2b}$, $IgG_3$, IgA, IgM, kappa and lambda light chains (BIO-RAD Mouse-Typer sub-isotyping kit, Richmond, Calif.).

Media. All cell cultures were in Dulbecco's modified Eagles medium (DMEM) supplemented with glutamine (10 mM), penicillin (100 U/ml), streptomycin (100 µg/ml), 2-mercaptoethanol ($5 \times 10^{-5}$M), non-essential amino acids (10 mM), sodium pyruvate (100 mM), HEPES buffer (0.18 mM) and 14% Fetal Bovine Serum (Hyclone Laboratories, Logan, Utah). Selection (HAT) medium contained in addition $1 \times 10^{-4}$M hypoxanthine, $1.6 \times 10^{-5}$M thymidine and $4 \times 10^{-7}$M aminopterin. Freezing medium contained 60% HT medium, 30% Fetal Bovine Serum and 10% DMSO (dimethylsulphoxide).

Purification of mouse IgG. The IgG fraction of the monoclonal antibody from ascites was purified by caprylic acid precipitation as described by Steinbuch et al, Arch. Biochem. Biophys. 134:279–284, 1969. The caprylic acid supernatant was further purified by FPLC, Mono Q column chromatography equilibrated with 50 mM Na acetate, pH=6.0 (adjusted with 50 mM acetic acid). IgG was eluted with 0–40% gradient (limiting buffer being 50 mM Na acetate, pH-6.0 with 1M NaCl. IgG was eluted at 14.2% salt. The purity was checked by SDS-PAGE.

SDS-PAGE and Immunoblotting. SDS-PAGE analysis was performed as described by Maizel, Methods Virol. 5:179–246, 1971, on 7.5% polyacrylamide mini-slab gels. Protein bands were stained with Coomasie blue. Electrophoretically separated proteins were transferred onto Immobilon membranes (Millipore Corporation, Bedford, Mass.) using a semi-dry electro-transblotter (Janssen Life Sciences, Piscataway, N.J.). Unreacted sites on the membranes were blocked with 5% dry skimmed milk solution in PBS (BLOTTO) for 1 hour at RT. The membranes were then incubated for 1 hour at RT with culture supernatants diluted 1:10 or purified monoclonal Ig at 1:2,000 in BLOTTO. After three washes with BLOTTO, Immobilon membranes were incubated with gold labeled goat-anti mouse IgG (Janssen Life Sciences, Piscataway, N.J.) for several hours to overnight at RT. After the final three washes in PBS, bands were visualized by incubating the membranes with silver enhancement solution (Catalog # B-2430, Janssen Life Sciences, Piscataway, N.J.).

RESULTS

Initial clones. A total of 5 antibody-producing clones from three separate cell fusions were identified by ELISA assay - four from the first fusion, one from the second and none from the third. Subsequent Western blotting of the culture supernatants of these clones with Immobilon strips to which human plasma proteins were transblotted from a non-reduced 7.5% SDS gel, showed that two of the clones reacted with sgp 120, while the remaining three clones demonstrated reactivity with a protein of apparent molecular weight of 130 kDa (FIG. 1). One of the clones was further expanded and subcloned, while the other positive clones were frozen in 10% DMSO medium and kept at −70° C.

Specificity of B1.9.E-2. After two consecutive phases of subcloning, the desired monoclonal antibody (designated B1.9.E-2) was characterized with respect to specificity in indirect ELISA and finally by immunoblotting on SDS gels of human plasma proteins. Both culture supernatant and fractionated ascites showed reactivity only with sgp 120 (FIG. 2).

A culture of hybridoma B1.9.E-2 was deposited on Mar. 2, 1992 in the American Type Culture Collection (ATTC), 12301 Parklawn Drive, Rockville, Md. 20852, and was given accession number HB 10978. All restrictions on the availability to the public to the culture so deposited will be irrevocably removed upon the granting of the patent.

Ig class and subclass characterization. Monclonal antibody B1.9.E-2 is of $IgG_1$/kappa isotype, as determined by ELISA Mouse-Typer sub-isotyping kit (BIO-RAD).

Reactivity with cleaved sgp 120. sgp 120 specifically cleaved with kallikrein was transferred to Immobilon and incubated with purified monoclonal IgG at 1:2,000 dilution. As shown in FIG. 3, the reactivity is evident only with 85 kDa and 60 kDa fragments, indicating that the epitope to which the monoclonal antibody binds is within the N-terminal portion of sgp 120.

Utilities. The availability of the monoclonal antibody B1.9.E-2 now allows simple purification of substantial amounts of sgp 120 by using standard immunoaffinity chromatographic techniques well known to one of ordinary skill in the art. Furthermore, by employing simple immunological, histological, radiological techniques and combinations thereof, the presence of sgp 120 can be easily detected and localized in biological samples such as cellular components, tissues, plasma and the like, both in vitro and in vivo. In addition, the specific binding property of B1.9.E-2 can be utilized to control the activity of sgp 120 by neutralizing the same with the antibodies.

In accordance with the present invention, a kit for detecting the presence of sgp 120 in a biological sample comprises a container containing anti-sgp 120 monoclonal antibody. A composition of matter in accordance with the present invention comprises sufficient amount of B1.9.E-2 monoclonal antibody to react with or inactivate sgp 120 in a suitable medium or carrier such as physiological saline, non-toxic buffer, pharmaceutically acceptable vehicle and the like as are well known to one of ordinary skill in the art.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. Hybridoma designated ATCC No. HB10978 secreting anti-sgp 120 monoclonal antibody.

2. Anti-sgp 120 monoclonal antibody secreted by the hybridoma of claim 1.

3. A method for localizing or detecting the presence of sgp 120, comprising reacting a cellular component, tissue or body fluid in which the presence of sgp 120 is to be ascertained, with the monoclonal antibody of claim 2, the occurrence of a positive immunological reaction being indicative of the presence of sgp 120.

4. A method for purification of sgp 120, comprising isolating sgp 120 from impurities by binding sgp 120 with the monoclonal antibody of claim 2 while removing the impurities, and then recovering substantially pure sgp 120 bound to said antibody.

5. A composition of matter comprising an immunoreactive amount of the monoclonal antibody of claim 2 and a non-toxic medium.

6. A kit for detecting the presence of sgp 120 comprising a container containing anti-sgp 120 monoclonal antibody of claim 2.

* * * * *